United States Patent [19]

Fuchs

[11] Patent Number: 4,599,199

[45] Date of Patent: Jul. 8, 1986

[54] OBTAINING CAPROLACTAM FROM EPSILON-AMINOCAPROIC ACID

[75] Inventor: Hugo Fuchs, Ludwigshafen, Fed. Rep. of Germany

[73] Assignee: BASF Aktiengesellschaft, Ludwigshafen, Fed. Rep. of Germany

[21] Appl. No.: 696,796

[22] Filed: Jan. 31, 1985

[30] Foreign Application Priority Data

Feb. 2, 1984 [DE] Fed. Rep. of Germany ....... 3403574

[51] Int. Cl.[4] ............................................. C07D 201/08
[52] U.S. Cl. ............................................... 260/239.3 A
[58] Field of Search ................................. 260/239.3 A

[56] References Cited

U.S. PATENT DOCUMENTS

| | | | |
|---|---|---|---|
| 2,956,051 | 10/1960 | Duxbury et al. | 260/239.3 A |
| 3,658,810 | 4/1972 | Tanaka et al. | 260/239.3 A |
| 3,988,319 | 10/1976 | Mares | 260/239.3 A |
| 4,360,461 | 11/1982 | Fuchs et al. | 260/234.3 A |

OTHER PUBLICATIONS

Tetrahedron Letters vol. 21, pp. 2443–2446 (Bladé-Font)

*Primary Examiner*—Robert T. Bond
*Attorney, Agent, or Firm*—Keil & Weinkauf

[57] ABSTRACT

Caprolactam is obtained by treating ε-aminocaproic acid with steam at elevated temperatures in the presence of a catalyst by a process in whcih ε-aminocaproic acid is introduced into a fluidized alumina bed and treated in the presence of steam at from 290° to 400° C.

5 Claims, No Drawings

OBTAINING CAPROLACTAM FROM EPSILON-AMINOCAPROIC ACID

In the preparation of caprolactam, the polycaprolactam initially obtained contains about 10% by weight of monomers and oligomers. The monomers and oligomers are extracted, with water, from the monomer-containing polycaprolactam, this being carried out by a conventional method. Caprolactam is recovered from such aqueous extracts by extraction with a solvent or by distillation. However, substantial amounts of residues which require treatment remain, these residues containing, inter alia, considerable amounts of aminocaproic acid.

Tetrahedron Lett. 21 (1980), 2443–2446, discloses a process for the preparation of caprolactam by treating aminocaproic acid in the presence of alumina, with continuous removal of the water formed in the procedure. This process is unsatisfactory industrially in that it requires a considerable time, e.g. 20 hours. In another process, disclosed in German Laid-Open Application DOS No. 1,944,910, caprolactam is obtained by treating $\epsilon$-aminocaproic acid with superheated steam at from 200° to 350° C. in the presence of an acidic catalyst, e.g. a phosphoric acid. The caprolactam obtained by the conventional process is still very impure and requires further expensive purification measures. In particular, the caprolactam obtained in this manner has a high permanganate titration number and a high characteristic UV number so that it cannot be worked up directly with crude caprolactam without substantially reducing the quality of the latter. It is therefore necessary for caprolactam obtained in this manner to be purified separately, which is technically very complicated.

It is an object of the present invention to design the preparation of caprolactam from $\epsilon$-aminocaproic acid in such a way that high yields are obtained in a short time, and at the same time caprolactam is obtained in a quality which permits it to be worked up, without disadvantages, together with crude caprolactam.

We have found that this object is achieved by a process for obtaining caprolactam by treating $\epsilon$-aminocaproic acid with steam at elevated temperatures and in the presence of a catalyst, wherein $\epsilon$-aminocaproic acid is introduced into a fluidized alumina bed and is treated in the presence of steam at from 290° to 400° C.

The novel process has the advantages that caprolactam is obtained in high yields, the process takes place in a short time and is simple to carry out, and the caprolactam obtained has a lower permanganate titration number and a lower characteristic UV number. Finally, the novel process is noteworthy in that it is not necessary to use pure $\epsilon$-aminocaproic acid as a starting material; instead, it is also possible to use $\epsilon$-aminocaproic acid containing oligomeric caprolactam, the latter also being cleaved to give caprolactam in the novel process.

According to the invention, $\epsilon$-aminocaproic acid is used as a starting material. To facilitate handling, it is also possible to employ aqueous solutions, e.g. 5–60 percent strength by weight solutions, of $\epsilon$-aminocaproic acid, but solid $\epsilon$-aminocaproic acid together with caprolactam, e.g. from 80 to 99% by weight of caprolactam, can be used. It is also possible to use distillation residues of aqueous extracts of the polycaprolactam after caprolactam has been distilled off. Such distillation residues contain not only $\epsilon$-aminocaproic acid but also caprolactam and its oligomers. As a rule, such oligomers have a degree of polymerization n of from 2 to 9. In particular, the said residues contain dimeric and trimeric cyclic oligomers. Suitable mixtures contain, for example, from 0.1 to 10% by weight of $\epsilon$-aminocaproic acid, from 40 to 95% by weight of caprolactam and from 5 to 50% by weight of oligomers.

The above mixtures are advantageously introduced into a fluidized alumina bed in liquid form, i.e. in the molten state or as a suspension in the melt, e.g. at from 150° to 250° C. However, it is also possible, as stated above, for the $\epsilon$-aminocaproic acid or mixtures containing this to be introduced into the fluidized bed in finely divided solid form, and to be converted to caprolactam monomer. Introduction into the fluidized bed is effected by, for example, blowing in by means of a nozzle operated with an inert gas.

Suitable aluminum oxides are the various modifications, such as alumina or boehmite, and $\gamma$-alumina has proven a particularly useful catalyst. The catalyst is kept fluidized with an inert gas, such as carbon dioxide, argon or nitrogen, preferably the last mentioned gas. The alumina used advantageously has a particle size of from 0.05 to 1.5, in particular from 0.2 to 1, mm. The height of the catalyst bed is advantageously chosen so that the residence time in this bed is from 0.1 to 30, in particular from 0.5 to 10, seconds. The process is advantageously carried out under atmospheric pressure, but may also be effected under slightly reduced or slightly superatmospheric pressure, e.g. as high as 2 bar.

The catalyst bed is kept at from 290° to 400° C., temperatures from 300° to 360° C. having proven particularly useful. It is therefore also advantageous for the inert gas to be fed at from 290° to 400° C. into the fluidized bed.

According to the invention, the treatment is carried out in the presence of steam. Advantageously, from 0.005 to 10, in particular from 0.02 to 2, parts by weight of water in the form of steam are used per part by weight of $\epsilon$-aminocaproic acid. If, as stated above, the starting mixtures contain oligomers, the stated amounts of water are based on the sum of $\epsilon$-aminocaproic acid and oligomers. The water used concomitantly can be introduced as such into the fluidized bed and vaporized there. However, the water is preferably fed in as steam, which, for example, can also be introduced into the fluidized bed together with the inert gas.

The gas mixture emerging from the fluidized bed is condensed in a bubble tray column by introducing water at the top of the column, as described in, for example, German Published Application DAS No. 1,445,549. Caprolactam is obtained as the bottom product, and the inert gas and steam emerge at the top of the column. The steam is advantageously condensed from the inert gas, and the latter is expediently recycled into the fluidized bed.

The condensed caprolactam is advantageously purified again, for example by distillation, and the caprolactam recovered in this manner is then added to the caprolactam which is obtained from the Beckmann rearrangement and is to be purified, the caprolactam from the two sources being worked up together, for example by the method described in German Patent No. 1,194,863.

However, it is also possible for the caprolactam to be condensed, as described above, from the vapor mixture emerging from the fluidized bed, and to be added directly to the crude lactam from the Beckmann rearrangement, and to work up the caprolactam from the two sources together.

Caprolactam is used for the preparation of polycaprolactam. The Examples which follow illustrate the process according to the invention.

EXAMPLE 1

In a vertical, insulated, electrically heated tube which has a length of 1,200 mm and a diameter of 100 mm and is provided below with a perforated base, 1,000 g of catalyst which consists of a γ-alumina calcined at 800° C. and having a particle size of from 0.2 to 0.8 mm are heated at 320° C.

The catalyst is fluidized by means of a stream of 2,500 l (S.T.P.)/h of nitrogen preheated to 360° C. and blown in from below through the perforated base. From a stock vessel heated at 170° C., 4,500 g/hour of a caprolactam/ε-aminocaproic acid/oligomer melt, or suspension in a melt, containing 5% (w/w) of ε-aminocaproic acid and 30% (w/w) of oligomers are sprayed into the catalyst bed with the aid of a stream of 1,500 l (S.T.P.)/h of nitrogen preheated to 200° C., through a two-material nozzle located concentrically in the tube, 90 mm above the perforated base, and pointing upward. 600 g/hour of steam are added to the preheated nitrogen stream, and the temperature in the catalyst bed is kept at 320° C. by means of the electric heater. The vapors leaving the reactor are condensed in a bubble tray column having a diameter of 100 mm and containing 10 trays, by adding water at the top of the column. In this manner, 4,300 g/hour of caprolactam which is free of aminocaproic acid and virtually free of oligomers are obtained. The characteristics of the resulting lactam are as follows, based on anhydrous lactam:

Permanganate titration number (PTN) 180
Characteristic UV number 520

500 g of this lactam are added to 5,000 g of extract lactam having the following characteristics:
PTN 50
characteristic UV number 110
volatile bases 0.6 meq/kg.

The lactam from the two sources are worked up together by distillation under reduced pressure to give pure lactam.

The resulting pure lactam has the following characteristics:

| Solidification point | 69.1° C. |
| --- | --- |
| PIN | 1.5 |
| Permanganate absorption number (PAN) | 3.8 |
| Characteristic UV number | 4.8 |
| Extinction at 290 nm for a 1 cm path length (50% strength aqueous solution) | 0.03 |
| Volatile bases | 0.15 meq/kg |

EXAMPLE 2

In an apparatus as described in Example 1, 1,000 g of γ-alumina, as a catalyst, are heated at 300° C. and fluidized with 2,500 l (S.T.P.)/h of nitrogen. A mixture of 200 g/hour of oligomers and 200 g/hour of ε-aminocaproic acid, in the form of a powder, is introduced into the hot catalyst bed via a nozzle operated with about 2,000 l (S.T.P.)/h of nitrogen. 2,000 g of steam are simultaneously introduced into the catalyst bed, together with the nitrogen necessary for fluidization. The vapor mixture leaving the reactor is condensed as described above.

350 g/hour of caprolactam monomer having the following characteristics are obtained:
PTN 300
characteristic UV number 400.

250 g of this lactam are worked up together with 2,500 g of extract lactam as described above to give pure lactam. The characteristics of the pure lactam are as follows:

| Solidification point | 69.12° C. |
| --- | --- |
| PIN | 1.6 |
| PAN | 4.2 |
| Characteristic UV number | 3.55 |
| Extinction at 290 nm for a 1 cm path length (50% strength aqueous solution) | 0.025 |
| Volatile bases | 0.11 meq/kg |

EXAMPLE 3

In an apparatus as described in Example 1, 1,000 g of γ-alumina, as a catalyst, are heated at 300° C. and fluidized with 2,500 l (S.T.P.)/h of nitrogen. 1,000 g/hour of a 40% strength (w/w) aqueous ε-aminocaproic acid solution are sprayed into the hot catalyst bed via a nozzle. The vapor mixture leaving the reactor is condensed as described above. After removal of the water, 304 g/hour of caprolactam are obtained from the resulting aqueous caprolactam solution; the caprolactam obtained has the following characteristics:
PTN: 270
characteristic UV number 520.

The lactam obtained could be worked up together with extract lactam as described above to give a pure on-spec lactam.

UV number

Principle:
The absorption of the caprolactam is measured in the spectral range from 360 to 270 nm and is converted to a characteristic parameter.

Analytical equipment:
1 recording spectrophotometer
1 200 ml conical flask
2 10 cm long quartz cells with lids (path length 10 cm).

Method:
50 g of caprolactam are dissolved in 50 g of doubly distilled cold water in a conical flask. One of the cells is filled with this solution up to the calibration mark. The second cell is filled with the same doubly distilled water, which constitutes the comparison solution.

The two cells are now closed with the lids, the ground surfaces are cleaned with tissue paper and the cells are inserted into the cell holders. The spectrum between 370 nm and 260 nm is then recorded in accordance with the operating instructions of the instrument. The recording speed is 50, and the extinction measurement is carried out in the measuring range from 0 to 1.

When the recording is complete, the paper is marked at 10 nm intervals from 270 to 360 nm.

Evaluation:
The extinctions at 270, 280, 290, 300, 310, 320, 330, 340, 350 and 360 nm are read off from the diagram and summed.

The sum of the 10 extinction values is multiplied by 2 to obtain the characteristic UV number. Hence, the latter is always based on 100% pure caprolactam and a path length of 10 cm.

To determine the volatile bases, 40 ml of 30% strength sodium hydroxide solution are introduced into a Kjeldahl apparatus, followed by a solution of 20 g of the substance in 80 ml of distilled water, and washing is carried out with 20 ml of distilled water. In the course of 5 minutes, while blowing in steam, 50 ml of water are then distilled into a vessel containing 5 ml of N/50 hydrochloric acid, 30 ml of water and 5 drops of indicator solution. The condenser together with the outlet tube is then washed with distilled water into the vessel, and the unconsumed acid is then backtitrated with N/50 sodium hydroxide solution. The amount of volatile bases in meq per kg of substance is obtained directly from the amount of N/50 hydrochloric acid consumed, taking into account the blank experiment.

The permanganate titration number, abbreviated to PTN, is the amount of N/10 potassium permanganate solution, in ml, consumed by a solution of 1,000 g of the substance in 2,500 g of 50% strength aqueous sulfuric acid until the permanganate color is stable for 2 minutes when the titration is carried out at room temperature.

Permanganate absorption number (PAN)

The extinction is determined, after 600 sec and at 420 nm, from the transmittance of a 1% strength caprolactam solution in water (50 ml or 100 ml of solution) after the addition of 0.01 N $KMnO_4$ solution (1 or 2 ml) at 25° C., in comparison with a solution which does not contain caprolactam but is otherwise identical.

We claim:

1. A process for obtaining caprolactam from ε-aminocaproic acid, which comprises treating ε-aminocaproic acid in a fluidized alumina bed in the presence of steam at from 290° to 400° C.

2. A process as claimed in claim 1, wherein from 0.005 to 10 parts by weight of water in the form of steam are used per part by weight of ε-aminocaproic acid.

3. A process as claimed in claim 1, wherein the temperature is kept at from 300° to 360° C.

4. A process as claimed in claim 1, wherein the ε-aminocaproic acid used additionally contains caprolactam and/or its oligomers.

5. A process as claimed in claim 1, wherein γ-alumina is used as the catalyst.

* * * * *